(12) United States Patent
Gray

(10) Patent No.: US 7,154,994 B2
(45) Date of Patent: Dec. 26, 2006

(54) SYNCHRONIZATION OF X-RAY DATA ACQUISITION

(75) Inventor: Keith Gray, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 305 days.

(21) Appl. No.: 10/823,923

(22) Filed: Apr. 14, 2004

(65) Prior Publication Data

US 2005/0232394 A1    Oct. 20, 2005

(51) Int. Cl.
*H05G 1/58*    (2006.01)
(52) U.S. Cl. .................. 378/116; 378/98.8; 250/370.09
(58) Field of Classification Search ............... 378/98.8, 378/116; 250/370.09
See application file for complete search history.

(56) References Cited

U.S. PATENT DOCUMENTS 5,027,380 A * 6/1991 Nishiki ........................ 378/4
5,436,952 A * 7/1995 Haendle et al. ............. 378/98.7
6,343,112 B1 * 1/2002 Petrick et al. ............. 378/98.9
6,459,765 B1 * 10/2002 Ganin et al. ................ 378/108
6,470,071 B1 * 10/2002 Baertsch et al. .............. 378/62

* cited by examiner

*Primary Examiner*—Courtney Thomas
*Assistant Examiner*—Thomas R. Artman
(74) *Attorney, Agent, or Firm*—Carr & Ferrell LLP

(57) ABSTRACT

Systems and methods of switching between data acquisition modes in an x-ray system are disclosed. The x-ray system includes a control device and a detector device, the detector device including one or more x-ray sensors. During changes in acquisition modes, responsibility for flushing the one or more x-ray sensors may be transferred from the control device to the detector device. When the detector device is ready to begin acquiring data in a new data acquisition mode, the responsibility is transferred back from the detector device to the control device.

24 Claims, 3 Drawing Sheets

SYNCHRONIZATION OF X-RAY DATA ACQUISITION

BACKGROUND

1. Field of the Invention

The invention is in the field of data acquisition, and more specifically in the field of detection systems.

2. Description of the Related Art

X-ray images may be recorded using a sensor array of charge coupled devices (CCDs). Charge coupled devices typically detect light by measuring collection of charge on a capacitor. Detectable photons increase the rate of charge collection and a measurement of the total charge collected within a period of time is indicative of a number of photons sensed. Typically, when charge collection is measured, the collected charge is allowed to escape (flushed) from the capacitor so that another charge collection and measurement cycle can begin. Charge collection and measurement cycles are sometimes referred to as data acquisition "frames."

Charge coupled devices normally have an internal dark current that results in a minimum charge collection rate that is independent of the presence of detectable photons. If the collected charge is not flushed periodically this dark current will result in an offset and eventual saturation of the sensor. Charge coupled devices configured for detection of x-rays are, therefore, regularly flushed. Flushing preferably occurs between periods of charge collection intended for photon measurement and may be required even when the sensor array is not in a photon detection mode.

In a typical array of charge coupled devices, flushing is controlled by an internal clock configured to generate an electrical signal called an internal sync pulse. The charge coupled devices are flushed whenever an internal sync pulse occurs. The internal sync pulse is typically also available as an output of the sensor array. This output allows other devices such as data acquisition systems and external control electronics to coordinate their activities with the sensor array. For example, the internal sync pulse is commonly used to indicate a start of a data acquisition frame (that includes activation of an x-ray source, and a charge collection and measurement cycle). Coordination between sensor flushing and data acquisition is important because it would be undesirable for the charge coupled devices to be flushed during periods of charge collection for measurement of x-rays. Conflicts between detector flushing and charge collection for measurement are avoided by having the external control electronics monitor the internal sync pulse. In alternative configurations, flushing is controlled by an external signal from the external control electronics. In these configurations, the external signal is used to trigger generation of internal sync pulses at times determined by the external control electronics.

The internal sync pulse is optionally also used for coordination of communication between an array of charge couple devices and external control electronics. For example, in some cases, timing of data transfer or command signals between the external control electronics and the array of charge couple devices is tied to the occurrence of internal sync pulses. In these cases, each transfer of data or command signal is timed according to an internal sync pulse. As a consequence, a series of commands and replies between the array of charge couple devices and the external control electronics may require a series of internal sync pulses and the time required for the series of commands and replies may be dependent on the frequency of internal sync pulses.

When the array of charge couple devices uses an external signal from external control electronics for generation of internal sync pulses, the timing of data acquisition events are controlled by the external control electronics. This relationship between the external control electronics and the array of charge couple devices may be characterized as a "master-slave" relationship, the external control electronics being the master and the array of charge couple devices being the slave. In other configurations or data acquisition modes, the external control electronics may operate as a slave to the array of charge couple devices.

This master-slave relationship can be a disadvantage when a data acquisition mode of the array of charge couple devices is changed. For example, a user may wish to change from a "normal fluoroscopy" mode to a "full resolution" mode. This data acquisition mode change may require that the operation of the charge couple devices be altered and that configuration data be communicated between the array of charge couple devices and external control electronics. Because the series of communications required for a change in data acquisition mode require a series of internal sync pulses and because there may be some time required for the array of charge couple devices to react to the communications, a data acquisition mode change may require that the array of charge couple devices be unavailable for data acquisition over a period of time during which several internal sync pulses would be generated. During and after the data acquisition mode change there may be an additional undesirable delay before the external control electronics and array of charge couple devices have reestablished their master-slave relationship and are thus sufficiently synchronized for data acquisition. The total delay resulting from communications requirements, reaction time, and resynchronization is a disadvantage of the prior art in that this delay reduces the possibility of being able to perform rapid changes between data acquisition modes. Rapid changes in data acquisition modes are desirable when, for example, a physician wishes to use a first mode for real time observation and a second mode for high resolution examination of an item of interest.

BRIEF DESCRIPTION OF THE VARIOUS VIEWS OF THE DRAWINGS

SUMMARY

Figure 1:
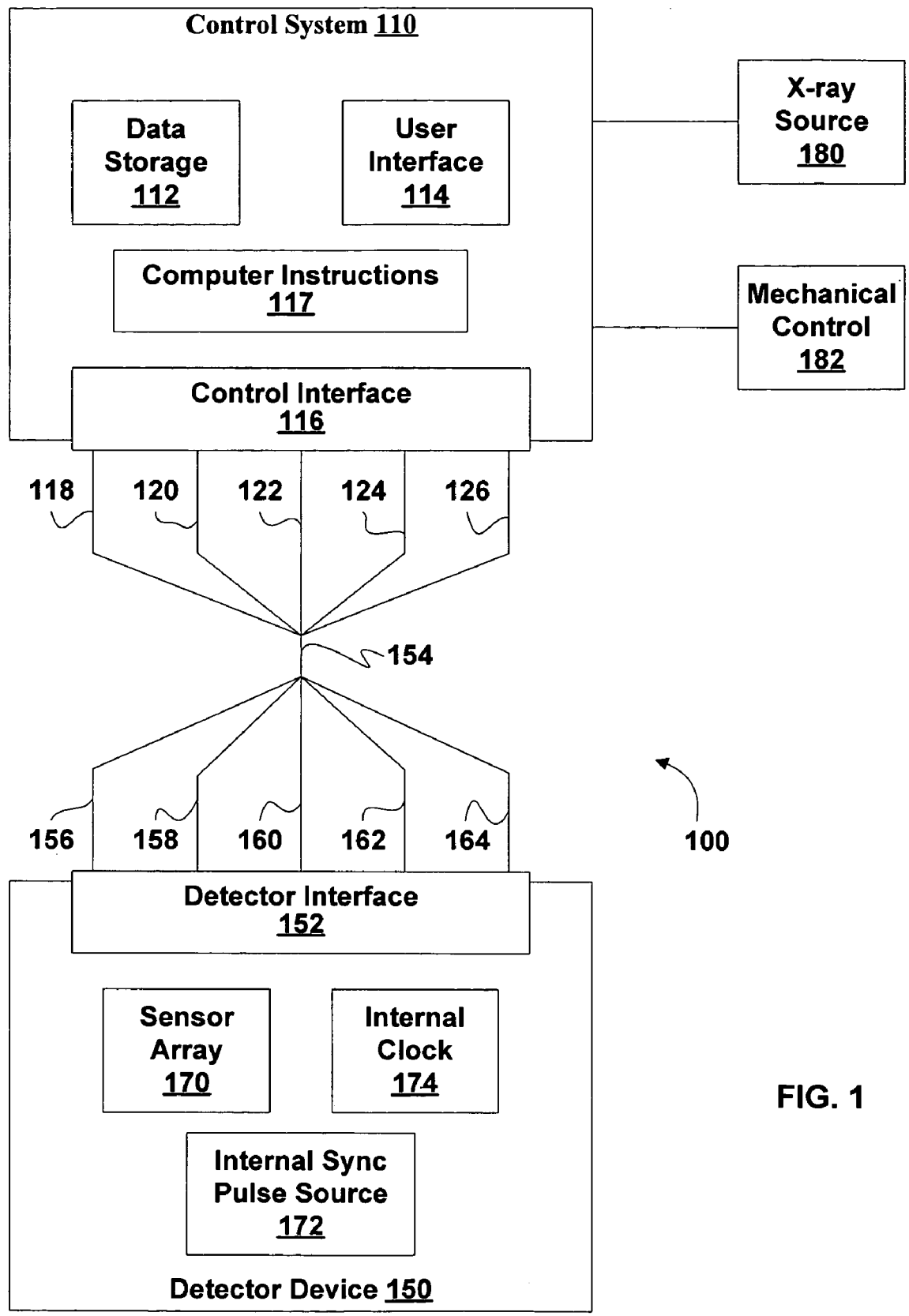
FIG. 1 is a block diagram of an x-ray system, according to various embodiments of the invention.

The present invention is directed to improved systems and methods relating to data acquisition. In some embodiments, these improvements reduce times required to change between data acquisition modes. For example, a physician, using the systems and methods of the invention may more conveniently switch between data acquisition modes while generating x-ray images. The invention is illustrated herein through embodiments including an x-ray system. However, further embodiments, including other types of data acquisition, are envisioned.

Various embodiments of the invention include a detector device comprising a sensor array configured to detect x-rays, an internal sync pulse source configured for flushing the sensor array, an internal clock configured for triggering the internal sync pulse source to generate an internal sync pulse, an external sync input configured for triggering the internal sync pulse source to generate the internal sync pulse, a ready signal output configured to indicate when the internal sync pulse is generated responsive to the internal clock and when the internal sync pulse can be generated responsive to the external sync input, and an input configured for initiating a data acquisition mode transition, the internal sync pulse being generated using the internal clock during at least part of the acquisition mode transition, the internal sync pulse being generated using the external sync input following to the data acquisition mode change.

Various embodiments of the invention include a detector device comprising an internal clock, a sensor array configured to acquire data in a first data acquisition mode and to acquire data in a second data acquisition mode, an input configured for initiating a data acquisition mode change between the first data acquisition mode and the second data acquisition mode, and an electronic circuit configured for flushing the sensor array responsive to the internal clock during at least part of the acquisition mode change and configured for flushing the sensor array responsive to an external signal prior to the data acquisition mode change.

Various embodiments of the invention include a control system comprising an interface configured for communication with an x-ray detector device, and computer instructions configured for communicating through the interface, the communication including an output signal configured to control frame start times of the x-ray detector device, an output signal configured to initiate a data acquisition mode transition of the x-ray detector device, an input signal, from the detector device, configured to indicate whether the frame start times are dependent or independent of the output signal configured to control frame start times.

Various embodiments of the invention include an x-ray system comprising a detector device including an array of sensors configured to detect x-rays, an output configured to indicate when an external sync input can be used to trigger internal sync pulses for indicating frame starts, and an internal circuit configured to flush the array of sensors responsive to an internal clock, the internal clock configured to trigger the internal sync pulses during at least part of a data acquisition mode change; and a control system including data storage configured to store x-ray data generated using the detector device, computer instructions configured to initiate the data acquisition mode change, an output configured to provide the external sync input to the detector device, an input configured to monitor the output of the detector device and detect the completion of the data acquisition mode change.

Various embodiments of the invention include a method of operating an x-ray system, the method comprising sending a plurality of first frame-start signals to a detector device, the first frame-start signals configured to determine frame starts in a first acquisition mode, sending a second signal to the detector device, the second signal configured to initiate a change in acquisition mode from the first acquisition mode to a second acquisition mode, receiving a third signal from the detector device, the third signal configured to indicate that the change in acquisition mode has begun and that a clock internal to the detector device is being used to flush a sensor array of the detector device, receiving a forth signal from the detector device, the forth signal indicating that the detector device is prepared to receive second frame-start signals, and sending a plurality of second frame-start signals to the detector device, the second frame-start signals configured to determine frame starts in a second acquisition mode.

Various embodiments of the invention include a method of operating detector device, the method comprising receiving, at the detector device, a prepare signal from a control system, the prepare signal configured to facilitate a change in acquisition mode from a first data acquisition mode to a second data acquisition mode, sending, from the detector device, a first signal to the control system, the first signal configured to indicate that generation of internal sync pulses is being triggered using a clock internal to the detector device, flushing one or more x-ray sensor using the internal sync pulses generated responsive to the clock, the one or more x-ray sensor being included in the detector device, sending a second signal, from the detector device, to the control system, the second signal configured to indicate that the detector device is prepared to receive frame-start signals, receiving the frame-start signals at the detector device, from the control system, using the frame-start signals, instead of the clock, to trigger generation of the internal sync pulses, and flushing the one or more x-ray sensor using the internal sync pulses generated responsive to the frame-start signals.

Various embodiments of the invention include an x-ray system comprising means for notifying a detector device of a pending change in data acquisition mode, means for generating an internal signal, the internal signal configured for assuring that x-ray sensors are flushed during at least part of the change in data acquisition mode, internal to the detector device, means for receiving an external signal, the external signal configured for assuring that x-ray sensors are flushed prior to or following the change in data acquisition mode, and means for switching between use of the internal signal and external signal, for assuring that the x-ray sensors are flushed.

These and other features, aspects, and advantages of the present invention will become better understood with reference to the following description and appended claims.

DETAILED DESCRIPTION OF THE INVENTION

Various embodiments of the invention include an external control system and an x-ray detector device configured for collecting x-ray image data using a detector array in a plurality of possible data acquisition modes. The x-ray detector device and the external control system are configured to change data acquisition modes more quickly than systems of the prior art. This improvement is accomplished using a "ready" signal to indicate when the x-ray detector device is prepared to accept external signals from the external control system for triggering of internal sync pulses. This indication facilitates resynchronization between the external control system and the x-ray detector device at or near the conclusion of a change in data acquisition mode, and thus reduces delays associated with the prior art.

For example, in some embodiments, a change in data acquisition mode includes a period during which internal sync pulses are generated by the x-ray detector device without the use of external signals from the external control system. This period is ended when the x-ray detector device uses the ready signal to indicate that it is prepared to accept external signals to trigger generation of internal sync pulses. When the external control system detects the ready signal it quickly responds by generating an external signal that triggers generation of an internal sync pulse. Thus, external control of internal sync pulse generation is established shortly after the x-ray detector device is prepared to accept external control, and delays previously associated with resynchronization are substantially eliminated. In some embodiments, transitions between acquisition modes are accomplished in less than four data acquisition frames.

In Various embodiments of the invention the ready signal may be configured for coordinating operation of the x-ray detector device and the external control system before, during and/or following changes in data acquisition mode. For example, in addition to reducing undesirable delays of the prior art, the ready signal and associated systems and methods, may be used for facilitating changes in master-slave relationships between the x-ray detector device and the external control system.

FIG. 1 is a block diagram of an X-ray System, generally designated 100, according to various embodiments of the invention. X-ray System 100 includes a Control System 110 and a Detector Device 150.

Control System 110 may be, for example, an external user console configured for a user to operate X-ray System 100. In a typical embodiment, Control System 110 includes Data Storage 112 configured to store data generated using Detector Device 150, a User Interface 114 configured for an operator to control X-ray System 100, a Control Interface 116 configured for communicating with Detector Device 150, and Computer Instructions 117 configured for, for example, communicating with Detector Device 150 through Control Interface 116. As discussed further herein, Control Interface 116 typically includes a Prepare Output 118, a Ready Input 120, an optional Internal Sync Input 122, an External Sync Output 124, and an optional Exposure Input 126.

Detector Device 150 includes a Detector Interface 152 configured to be coupled to Control Interface 116 through a Data Conduit 154. Detector Interface 152 includes a Prepare Input 156, a Ready Output 158, an optional Internal Sync Output 160, an External Sync Input 162, and an optional Exposure Output 164. These inputs and outputs of Detector Interface 152 correspond to the respective outputs and inputs of Control Interface 116. Data Conduit 154 is electronic, optical, or wireless.

Detector Device 150 further includes a Sensor Array 170, an Internal Sync Pulse Source 172, and an Internal Clock 174. Sensor Array 170 typically includes an array of x-ray detectors configured to generate data that can be used by Control System 110 to form an x-ray image. For example, Sensor Array 170 may include a plurality of charge coupled devices configured to measure x-rays by integrating charge collected over a period of time. Internal Sync Pulse Source 172 is used to generate internal sync pulses configured for causing flushing of Sensor Array 170. As discussed further herein, under some circumstances Internal Sync Pulse Source 172 generates internal sync pulses responsive to Internal Clock 174, and under some circumstances Internal Sync Pulse Source 172 generates internal sync pulses responsive to input received at External Sync Input 162. The frequency of internal sync pulse generation by Internal Sync Pulse Source 172 may depend on a current data acquisition mode and typically determines a current frame rate. An output of Internal Sync Pulse Source 172 is optionally available at Internal Sync Output 160.

In some embodiments, X-ray System 100 further includes an X-ray Source 180 and/or a Mechanical Control 182. X-ray source 180 includes a source of x-rays to be detected using Detector Device 150. Mechanical Control 182 includes systems for moving X-ray Source 180 and/or Detector Device 150. For example, in one embodiment, Mechanical Control 182 is configured to move X-ray Source 180 and Detector Device 150 relative to an object under analysis. In this embodiment, Mechanical Control 182 and Computer Instructions 117 are optionally configured to move X-ray Source 180 and Detector Device 150 after a predetermined number of frames have been recorded. X-ray Source 180 and Mechanical Control 182 operate responsive to Computer Instructions 117.

Figure 2:
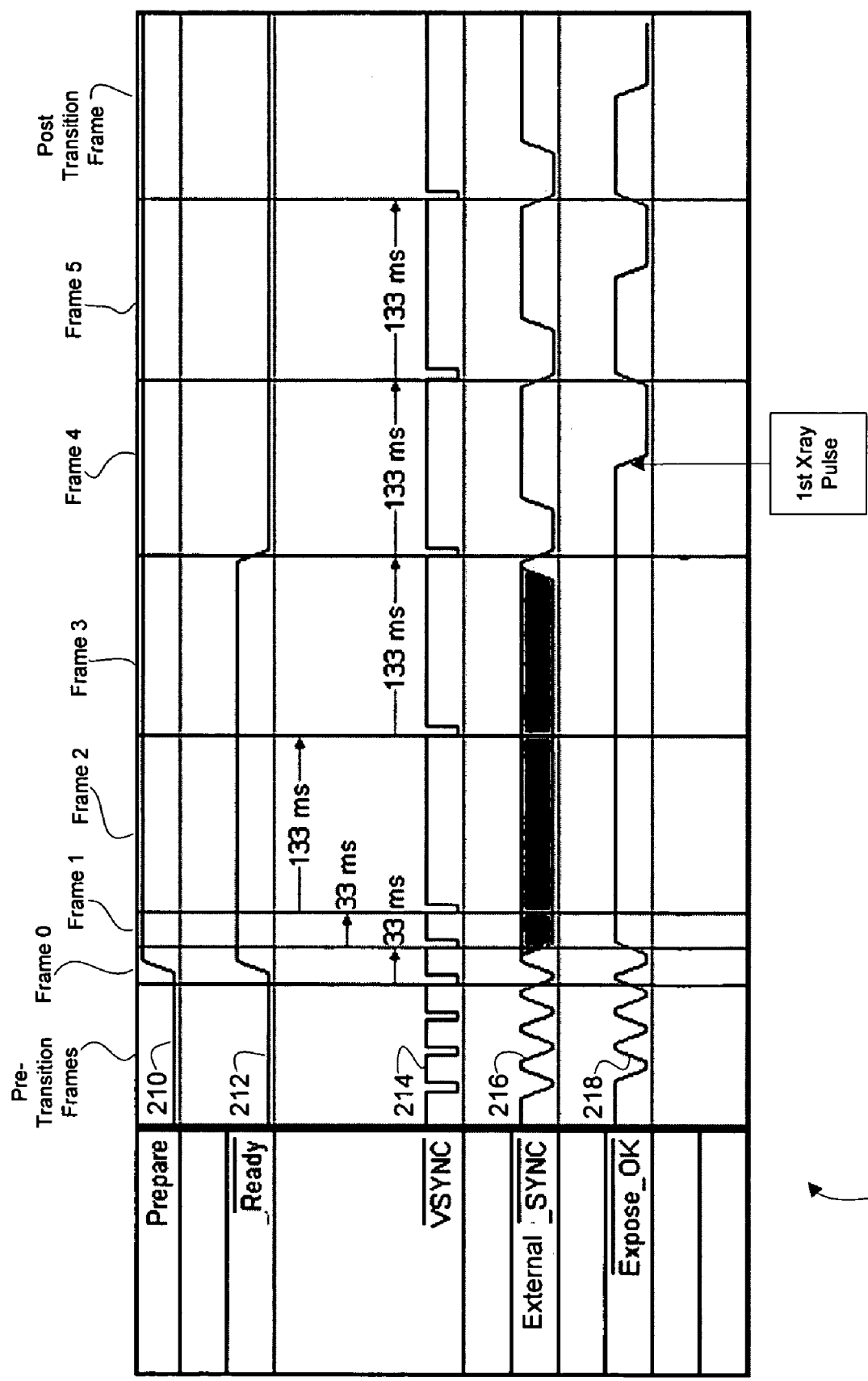
FIG. 2 is a timing diagram, according to various embodiments of the invention.

FIG. 2 includes a Timing Diagram 200 illustrating a process of changing data acquisition modes, according to various embodiments of the invention. For the purposes of illustration, FIG. 2 is presented with the assumption that the change in data acquisition modes is from a first mode described as "Normal Fluoroscopy" to a second data acquisition mode described as "Full Resolution Fluoroscopy." These modes involve different frame rates and different X-ray image resolutions. In the example shown, the Normal Fluoroscopy mode uses a 30 frames per second data acquisition rate and the Full Resolution Fluoroscopy mode uses a 7.5 frames per second data acquisition rate. The Full Resolution Fluoroscopy mode also uses a lower number of pixels per final image data point than does the Normal Fluoroscopy mode. The number of pixels per image data point can be partially a result of data acquisition processes within Detector Device 150.

Timing Diagram 200 shows five signals as received or provided by Detector Interface 152. These signals include a Prepare Signal 210 received via Prepare Input 156, a Ready Signal 212 provided via Ready Output 158, a VSYNC Signal 214 provided via Internal Sync Output 160, an External Sync Signal 216 received via External Sync Input 162, and an Expose_OK Signal 218 provided via Exposure Output 164.

The x-axis of Timing Diagram 200 is a time axis divided into a Pre-Transition Frames region, six frames (Frame 0 through Frame 5), and a Post Transition Frame region. Each frame start is indicated by a falling edge (HIGH to LOW transition) of VSYNC Signal 214. Thus, the Pre-Transition Frames region (as shown) includes three full frames and Frame 0 starts with the fourth falling edge of VSYNC Signal 214. In the Pre-Transition Frames region Detector Device 150 is operating in the first data acquisition mode. In this mode Detector Device 150 is receiving External Sync Signal 216 every 33 milliseconds. The falling edge of External Sync Signal 216 controls the generation of internal sync pulses by Internal Sync Pulse Source 172. The timing of the internal sync pulses can be monitored at the VSYNC Signal 214 as shown in FIG. 2. In the Pre-Transition Frames region, Detector Device 150 operates as a slave to Control System 110. Detector Device 150 uses Exposure Output 164 to provide Expose_OK Signal 218 to Control System 110 at a suitable delay time after the frame start (falling edge of VSYNC Signal 214). Control System 110 may monitor this signal in order to determine when to generate x-rays using X-ray Source 180.

In frame 0 the transition between a first data acquisition mode and a second data acquisition mode begins. This transition is initiated by Prepare Signal 210, which is received from Control System 110. In response to a rising edge in Prepare Signal 210, Detector Device 150 prepares to receive instructions for a new data acquisition mode and prepares to switch to internal triggering of internal sync pulses, as observed at VSYNC Signal 214. When ready, and in response to the Prepare Signal 210, Detector Device 150 signals to Control System 110 that Detector Device 150 is ready to start the transition. This signal is conveyed using a rising edge in Ready Signal 212. By raising the level of Ready Signal 212, Detector Device 150 indicates that it is ready to receive mode transition instructions (configuration data) and that internal sync pulses are now generated responsive to Internal Clock 174 rather than External Sync Signal 216. (The mode transition instructions are transmitted from Control System 110 to Detector Device 150 during Frames 1–3, optionally through communication conduits not shown.) While Ready Signal 212 is high, External Sync Signal 216 is typically ignored by Detector Interface 152 and internal sync pulses are generated internally responsive to Internal Clock 174. This is indicated by the grayed out region of External Sync Signal 216 as shown in FIG. 2. Thus, which signal is used to determine frame start times is dependent on a state of Ready Signal 212. As described further herein, while Ready Signal 212 is high, some aspects of a master-slave relationship between Control System 110 and Detector Interface 152 are typically suspended.

Among the mode transition instructions received during Frame 1 or Frame 2 are instructions that cause Internal Sync Pulse Source 172 to generate the internal sync pulse every 133 milliseconds (7.5 Hz) instead of every 33 milliseconds (30 Hz). This change can be observed at the VSYNC Signal 214. Thus, Frame 1 is 33 milliseconds long and Frame 2 is 133 milliseconds long. Depending on the particular mode transition instructions communicated to Detector Device 150, one or more additional frames may be required to fully prepare Detector Device 150 to acquire data in the new data acquisition mode.

In the example illustrated in FIG. 2, Detector Device 150 becomes ready to acquire data in the second data acquisition mode at some time during Frame 3. This ready state is indicated by a falling edge in Ready Signal 212 generated by Detector Device 150 at Detector Interface 152. This falling edge is detected by Control system 110 through Control Interface 116. Control System 110 responds by providing a falling edge in External _Sync Signal 216, thus indicating a new frame start under the control of Control System 110. In turn, Detector Device 150 generates an internal sync pulse (observable on VSYNC Signal 214 at Internal Sync Output 160). This internal sync pulse starts Frame 4 under the control of Control System 110. The signal changes that occur near the start of Frame 4 allow Control System 110 to take control of the Detector Device 150 through External Sync Signal 216. A master-slave relationship between Control system 110 and Detector Device 150 may be reestablished before or at the start of Frame 4.

As shown in FIG. 2, some time later Expose_OK Signal 218 is used to activate X-ray Source 180. The data acquisition process can then continue in the second data acquisition mode as shown in the Post Transition Frame of FIG. 2.

Figure 3:
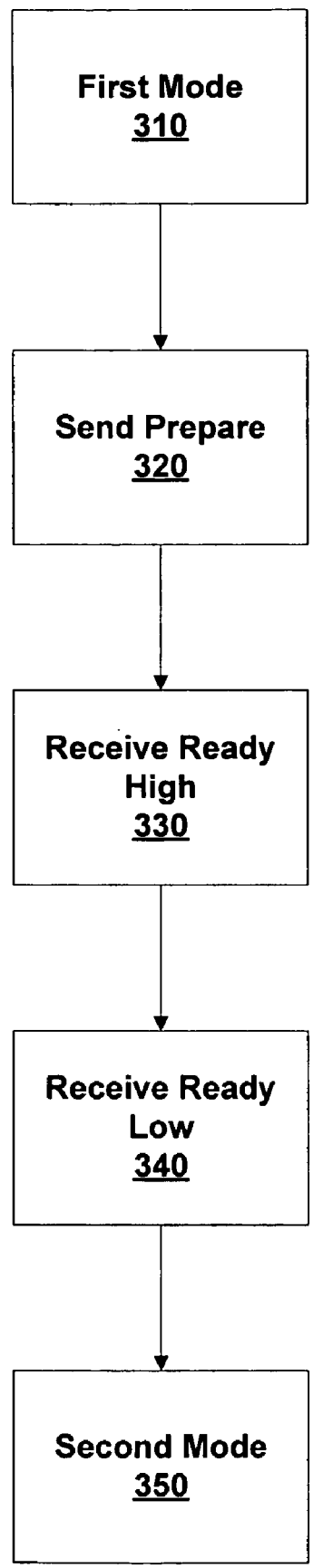
FIG. 3 is a flow chart illustrating a method, according to various embodiments of the invention.

FIG. 3 is a flow chart illustrating a method according to various embodiments of the invention. In a First Mode Step 310, X-ray System 100 operates in a first data acquisition mode. While operating in this mode, Control System 100 sends a plurality of first frame-start signals (for example, falling edges of External Sync Signal 216) to Detector Device 150; the first frame-start signals control the starting times of data acquisition frames and, thus, the data acquisition frame rate. Within each data acquisition frame x-ray data may be generated and transferred from Detector Device 150 to Control System 110.

In a Send Prepare Step 320, a signal is sent from Control System 110 to Detector Device 150 indicating that there may be a change in data acquisition mode. For example, in some embodiments of Send Prepare Step 320, Prepare Signal 210 is sent from Control System 110 to Detector Device 150. The signal sent in Send Prepare Step 320 is configured to initiate a change in acquisition mode from the first data acquisition mode to a second data acquisition mode.

In a Receive Ready High Step 330, Control System 110 receives a signal from Detector Device 150 indicating that the change in acquisition mode has begun and that Internal Sync Pulse Source 172 is generating internal sync pulses responsive to Internal Clock 174 rather than External Sync Signal 216. This received signal is, for example, Ready Signal 212. The internal sync pulses generated responsive to Internal Clock 174 are used to cause flushing of Sensor Array 170 during the change in data acquisition mode.

In a Receive Ready Low Step 340, Control System 10 receives a signal from Detector Device 150 indicating that Detector Device 150 is prepared to receive further frame-start signals for operation in the second data acquisition mode. The signal received in Receive Ready Low Step 340 may be, for example, a falling edge in Ready Signal 212. In response to receiving this signal, Control System 110 takes control of the timing of internal sync pulses within Detector Device 150 by sending a falling edge in External Sync Signal 216. This falling edge causes Internal Sync Pulse Source 120 to generate an internal sync pulse that results in flushing of Sensor Array 170, determines the start of a new data acquisition frame, and/or can be monitored at Internal Sync Output 160.

Between Receive Ready High Step 330 and Receive Ready Low Step 340, further data is typically transferred between Control System 110 and Detector Device 150. As discussed elsewhere herein, this data may be used to determine operating parameters of Detector Device 150 related to the second data acquisition mode. This data may include, for example, a new frame rate, a new image resolution, new calibration or offset parameters, or the like. VSYNC Signal 214, generated responsive to Internal Clock 174, is optionally used to facilitate this communication.

In a Second Mode Step 350, Control System 100 optionally sends a plurality of frame-start signals to Detector Device 150 in order to acquire x-ray data using the second data acquisition mode. These frame-start signals determine the data acquisition frame rate. In the second data acquisition mode communication between Control system 110 and Detector Interface 152 is optionally facilitated by External Sync Signal 216, or other signals derived therefrom.

In various embodiments of the invention, one or more master-slave relationships between Detector Device 150 and Control System 152 are altered as a consequence of switching between data acquisition modes and/or responsive to Ready Signal 212. For example, in some instances External Sync Signal 216 received by Detector Device 150 from Control System 152 is used to determine frame start times during x-ray data acquisition prior to a data acquisition mode transition. Under these conditions Detector Device 150 functions as a slave to Control System 152. During at least part of the subsequent data acquisition mode transition an internal clock signal of Detector Device 150 is used to determine frame start times, without the use of the External Sync Signal 216. Thus, with regard to at least this aspect of the relationship between Control System 152 and Detector Device 150, the previously existing maser-slave relationship has been altered. During the data acquisition mode transition, the operation of Control System 152 is optionally restricted by Ready Signal 212 received from Detector Device 150. Thus, during at least part of the data acquisition mode transition aspects of Control System 152 may be operated as slaves to Detector Device 150. Following the data acquisition mode transition, the original master-salve relationship between Control System 152 and Detector Device 150 is optionally reestablished.

Several embodiments are specifically illustrated and/or described herein. However, it will be appreciated that modifications and variations are covered by the above teachings and within the scope of the appended claims without departing from the spirit and intended scope thereof. For example, the various signals described herein may be communicated through alternative configurations of inputs and outputs. The approach to detector control described herein may be applied to other types of integrating detectors including those configured for detecting other wavelengths of light, for measuring currents or voltages, or for measuring transient physical properties. In some embodiments, Control system 110 and Detector Device 150 are combined in a single unit and Data Conduit 154 is internal. In some embodiments, transitions between data acquisition modes are coordinated with use of Mechanical Control 182 to move X-ray Source 180 and/or Detector Device 150. In some embodiments, the master-slave relationship between Control System 110 and Detector Device 150 is reversed in the second data acquisition mode relative to the first data acquisition mode.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The invention claimed is:

1. A detector device comprising:
a sensor array configured to detect x-rays;
an internal sync pulse source configured for flushing the sensor array;
an internal clock configured for triggering the internal sync pulse source to generate an internal sync pulse;
an external sync input configured for triggering the internal sync pulse source to generate the internal sync pulse;
a ready signal output configured to indicate when the internal sync pulse is generated responsive to the internal clock and when the internal sync pulse can be generated responsive to the external sync input; and
an input configured for initiating a data acquisition mode transition, the internal sync pulse being generated using the internal clock during at least part of the acquisition mode transition, the internal sync pulse being generated using the external sync input following to the data acquisition mode transition.

2. The detector device of claim 1, wherein the acquisition mode transition includes a change in data acquisition frame rate.

3. The detector device of claim 1, wherein internal sync pulse is generated using the external sync input prior to the data acquisition mode transition.

4. A detector device comprising:
an internal clock;
a sensor array configured to acquire data in a first data acquisition mode and to acquire data in a second data acquisition mode;
an input configured for initiating a data acquisition mode change between the first data acquisition mode and the second data acquisition mode; and
an electronic circuit configured for flushing the sensor array responsive to the internal clock during at least part of the acquisition mode change and configured for flushing the sensor array responsive to an external signal prior to the data acquisition mode change.

5. The detector device of claim 4, wherein the data acquisition mode change is performed in less than four data acquisition frames.

6. The detector device of claim 4, wherein the sensor array is configured to detect x-rays.

7. A control system comprising:
an interface configured for communication with an x-ray detector device; and
computer instructions stored on a computer readable medium, the computer instructions configured for communicating through the interface, the communication including
an output signal configured to control frame start times of the x-ray detector device,
an output signal configured to initiate a data acquisition mode transition of the x-ray detector device,
an input signal, from the detector device, configured to indicate whether the frame start times are dependent or independent of the output signal configured to control frame start times.

8. The control system of claim 7, wherein the x-ray detector device includes an array of integrating sensors requiring flushing.

9. The control system of claim 7, wherein the computer instructions are configured to control the x-ray detector device in a master-slave relationship prior to the data acquisition mode transition, and to reestablish the master-slave relationship following the data acquisition mode transition.

10. An x-ray system comprising:
a detector device including an array of sensors configured to detect x-rays,
an output configured to indicate when an external sync input can be used to trigger internal sync pulses for indicating frame starts, and
an internal circuit configured to flush the array of sensors responsive to an internal clock, the internal clock configured to trigger the internal sync pulses during at least part of a data acquisition mode change; and
a control system including
data storage configured to store x-ray data generated using the detector device,
computer instructions configured to initiate the data acquisition mode change,
an output configured to provide the external sync input to the detector device,
an input configured to monitor the output of the detector device and detect the completion of the data acquisition mode change.

11. The x-ray system of claim 10, further including a data conduit configured for communicating signals from the detector device to the control system.

12. The x-ray system of claim 10, further including an x-ray source and computer instructions configured to activate the x-ray source responsive to the frame starts.

13. The x-ray system of claim 10, further including an x-ray source and mechanical control configured to move the x-ray source.

14. The x-ray system of claim 10, wherein the computer instructions are further configured to change a master-slave relationship between the detector device and the control system during the acquisition mode change.

15. A method of operating an x-ray system, the method comprising:
   sending a plurality of first frame-start signals to a detector device, the first frame-start signals configured to determine frame starts in a first acquisition mode;
   sending a second signal to the detector device, the second signal configured to initiate a change in acquisition mode from the first acquisition mode to a second acquisition mode;
   receiving a third signal from the detector device, the third signal configured to indicate that the change in acquisition mode has begun and that a clock internal to the detector device is being used to flush a sensor array of the detector device;
   receiving a fourth signal from the detector device, the fourth signal indicating that the detector device is prepared to receive second frame-start signals; and
   sending a plurality of second frame-start signals to the detector device, the second frame-start signals configured to determine frame starts in a second acquisition mode.

16. The method of claim 15, wherein the first frame starts determine a first frame rate and the second frame starts determine a second frame rate.

17. The method of claim 15, wherein the change in acquisition mode includes a change in data acquisition frame rate.

18. The method of claim 15, wherein the change in acquisition mode is performed in less than four data acquisition frames.

19. A method of operating detector device, the method comprising:
   receiving, at the detector device, a prepare signal from a control system, the prepare signal configured to facilitate a change in acquisition mode from a first data acquisition mode to a second data acquisition mode;
   sending, from the detector device, a first signal to the control system, the first signal configured to indicate that generation of internal sync pulses is being triggered using a clock internal to the detector device;
   flushing one or more x-ray sensor using the internal sync pulses generated responsive to the clock, the one or more x-ray sensor being included in the detector device;
   sending a second signal, from the detector device, to the control system, the second signal configured to indicate that the detector device is prepared to receive frame-start signals;
   receiving the frame-start signals at the detector device, from the control system;
   using the frame-start signals, instead of the clock, to trigger generation of the internal sync pulses; and
   flushing the one or more x-ray sensor using the internal sync pulses generated responsive to the frame-start signals.

20. The method of claim 19, further including
   generating further internal sync pulses responsive to frame-start signals received from the control system prior to receiving the prepare signal, and
   flushing the one or more x-ray sensor using the internal sync pulses generated to the frame-start signals received from the control system prior to receiving the prepare signal.

21. The method of claim 19, further including receiving a command to change a frame rate, from the control system.

22. The method of claim 19, wherein the change in acquisition mode includes a change in data acquisition frame rate.

23. The method of claim 19, wherein the change in acquisition mode is performed in less than four data acquisition frames.

24. An x-ray system comprising:
   means for notifying a detector device of a pending change in data acquisition mode;
   means for generating an internal signal, the internal signal configured for assuring that x-ray sensors are flushed during at least part of the change in data acquisition mode, internal to the detector device;
   means for receiving an external signal, the external signal configured for assuring that x-ray sensors are flushed prior to or following the change in data acquisition mode; and
   means for switching between use of the internal signal and external signal, for assuring that the x-ray sensors are flushed.

* * * * *